United States Patent [19]

Patterson

[11] 4,203,726

[45] May 20, 1980

[54] THERMIONIC DETECTOR

[75] Inventor: Paul L. Patterson, Walnut Creek, Calif.

[73] Assignee: Varian Associates, Inc., Palo Alto, Calif.

[21] Appl. No.: 882,033

[22] Filed: Feb. 28, 1978

[51] Int. Cl.² .......................................... G01N 27/62
[52] U.S. Cl. .................................. 23/232 E; 73/23; 73/26; 324/468; 422/98; 422/54
[58] Field of Search ............. 23/232 R, 232 E, 254 E, 23/254 EF; 324/33; 73/23, 26; 422/54, 98

[56] References Cited

U.S. PATENT DOCUMENTS

| | | | |
|---|---|---|---|
| 3,372,994 | 3/1968 | Giuffrida | 23/254 EF |
| 3,423,181 | 1/1969 | Dimick et al. | 23/254 EF |
| 3,439,262 | 4/1969 | Roberts | 324/33 |
| 3,540,851 | 11/1970 | Vree et al. | 324/33 X |
| 3,547,588 | 12/1970 | Miyamoto et al. | 23/232 E |
| 3,589,869 | 6/1971 | Scolnick | 23/254 EF |
| 3,795,716 | 6/1957 | Roberts | 324/33 X |
| 3,852,037 | 12/1974 | Kolb et al. | 422/54 |
| 3,925,023 | 12/1975 | Kaiser | 23/254 EF |
| 4,047,101 | 9/1977 | Baurle et al. | 324/33 |

FOREIGN PATENT DOCUMENTS

| | | | |
|---|---|---|---|
| 335604 | 5/1972 | U.S.S.R. | 23/254 EF |
| 496488 | 3/1976 | U.S.S.R. | 23/254 EF |

Primary Examiner—Michael S. Marcus
Attorney, Agent, or Firm—Stanley Z. Cole; Peter J. Sgarbossa

[57] ABSTRACT

An instrument for the analysis of a sample material to detect the presence of specific substances that thermally decompose into electronegative species comprises a sensitized surface, means for heating the sensitized surface in a gaseous environment to generate a gaseous boundary layer adjacent the sensitized surface, means for causing the sample material to interact with the sensitized surface to form negative ions, a collector electrode maintainable at a different electrical potential from the sensitized surface to cause a current of these negative ions to the collector electrode, and means for measuring the ion current. The sensitized surface is formed on a ceramic body that is impregnated with an alkali metal. The composition and temperature of the sensitized surface, and the composition of the gaseous boundary layer are selected according to the specific substance to be detected.

54 Claims, 2 Drawing Figures

THERMIONIC DETECTOR

BACKGROUND OF THE INVENTION

1. Field of the Invention

This is a further development in thermionic detection techniques, and provides a method and apparatus for flameless thermionic detection of specific substances that thermally decompose into electronegative species.

2. Prior Art

In 1936, J. P. Blewett (Physical Review, Vol. 50, p. 464, 1936) described studies in which efficient filament sources of positive ions of the alkali metals were produced by heating synthetic alkali aluminum silicates. These alkali-glass sources were shown to be abundant emitters of positive ion current and poor emitters of negative ion current, especially when heated to temperatures close to the melting temperature of the alkali-glass.

In 1951, Rice (U.S. Pat. No. 2,550,498) described a method and apparatus for electrically detecting vapors of certain substances by sensitizing a hot surface with a material from the class of alkali metals and their compounds, bringing sample vapor into contact with the hot surface, and measuring the current of positive ions produced at the hot surface by the presence of the sample vapor. A preferred embodiment of Rice's apparatus consisted of two concentric platinum cylinders with appropriate diameters such that gas vapors of interest could flow through a gap between the inner and outer cylinders. The cylinders were electrically biased so as to cause the motion of positive ion current in the direction from the inner cylinder to the outer cylinder. The inner cylinder further surrounded a helical heater coil wound on an alumina cylinder. Natural alkali impurities within the alumina ceramic served to produce the required sensitizing action for a relatively short operating time. Rice taught that the active life of a sensitized alumina could be increased or restored by soaking the alumina in a water solution containing an alkali metal salt. For even longer life, Rice further taught that the alumina cylinder could be replaced by a cylinder of alkali glass such as one of those described by Blewett. The detector described by Rice was found to be especially effective in the detection of compounds containing halogen atoms.

In 1957, Roberts (U.S. Pat. No. 2,795,716) described an improved electrical vapor detector which used a positive ion source that provided a relatively long life compared to that source described in the Rice patent. The positive ion source described by Roberts consisted of a cylindrical alumina ceramic core upon which was wound a heater coil. The alumina core and heater coil were covered on their outer surfaces with a coating of positive ion emitting material. For the positive ion emitting material, Roberts used the alkali-glasses described by Blewett. The alkali-glass was powdered and mixed with a suitable ceramic cement in the desired proportion, and the mixture was coated on the alumina core and heater coil and allowed to set.

In 1975, Kolb and Bischoff (U.S. Pat. No. 3,852,037) described a selective ionization detector which used an electrically-heated alkali-galss bead maintained in a heated softened state during operation of the detector. Kolb and Bischoff theorized that the softened glass state acted to maintain an adequate supply of alkali to the surface of the glass by means of molecular motion within the body of the glass. Kolb and Bischoff described a detector in which the alkali glass bead was mounted above a burner nozzle to which a mixture of a combustible gas and a sample gas was supplied. A collecting electrode was located above the glass bead, with an electrical bias applied between bead and collector so as to direct negative ion current to move from the bead to the collector. Kolb and Bischoff further taught that specificity for particular individual substances could be obtained by suitable selection of gas flows and by selection of the appropriate alkali metal used in the alkali-glass bead. For example, rubidium-glass appeared best suited for detection of nitrogen compounds, whereas sodium-glass was especially good for phosphorus compounds.

In 1977, Burgett et al. (Journal of Chromatography, Vol. 134, p. 57, 1977), described a new nitrogen-phosphorus detector for gas chromatography. The active component in this detector was described as a ceramic cylinder coated with an alkali salt activator similar to that described by Rice. Actually, this alkali-ceramic cylinder has the physical appearance of a ceramic core covered by a glass-like outer shell, similar to the positive ion source described by Roberts. Like Rice and Roberts, the alkali-ceramic cylinder in Burgett's detector was suspended in the center of a collector cylinder and positive ion current arriving at the collector was measured. Electrically, one end of Burgett's alkali-cylinder was connected to the collector cylinder, and the other end was connected to a source of electrical heating power. The electrical potential difference between the alkali cylinder and the collector electrode was mostly provided by an electrical fringe field caused by biasing the collector at a high voltage with respect to a flame jet structure external to the collector.

The nature of the ionization mechanism operating in these prior art devices has not been well established. However, both Rice and Kolb and Bischoff theorized that the probable ionization mechanism involved release of neutral alkali atoms from the alkali source and subsequent gas phase ionization of the alkali vapors by reaction with sample compounds. Consequently, according to prior art teachings, the alkali source was considered as serving mainly to supply neutral alkali vapors to the gaseous environment of the source.

Those devices of the prior art which sensed positive ion current suffered from the fact that when heated, the alkali-sensitized sources were themselves abundant positive ion emitters even without the presence of a sample. Consequently, there always existed in these positive ion detectors a large background signal which acted to mask the responses obtained from samples. This high background level also was highly susceptible to noise variations caused by changes in such things as gas flows or contamination.

The devices described by Rice, Roberts, and Burgett et al. involved sensitized elements in which only the surface layers contained the activating alkali compound. Consequently, the lifetimes of these sensitized elements were limited by the depletion of active material from the surface layers.

In the alkali-glasses described by Blewett and Kolb and Bischoff, the alkali metal was present throughout the body of the glass; and Kolb and Bischoff theorized that active material in the glass surface layer was continually replenished by migration of alkali atoms from within the body of the glass. However, such synthetic alkali-glasses are difficult to manufacture because a glass melt must be made starting from dry ingredients. Furthermore, if a particular shape of the alkali-glass bead is desired, that shape must be formed while working with the glass in the molten state. A special complication in manufacturing, forming, and operating alkali-glass beads is the fact that the softening and melting points of the glass depend strongly on the type and density of the alkali metal used in the glass formulation. This property severely limits the freedom of manufacturing alkali-glass beads of widely varying formulations. In general, increasing the alkali atom content of a glass usually results in a decrease in melting point. Consequently, alkali-glass beads are often restricted in use at high temperatures due to the onset of glass melting. In fact, Kolb and Bischoff have taught that the alkali-glass beads in their device must be operated above the glass softening point for satisfactory operation. In the Kolb and Bischoff device, only a slight overheating of the bead is often sufficient to cause physical destruction of the bead by melting.

In the devices described by Kolb and Bischoff, and by Burgett et al., the electric field established between the alkali-bead and the collector electrode is highly non-uniform, and may appropriately be described as an electrical fringe field. As a consequence, the response characteristics of these two prior art devices are known to be highly dependent on the precise spatial location of the alkali-bead with respect to the collector or any other electrode that is at a different voltage from the bead.

SUMMARY OF THE INVENTION

This invention provides a thermionic ionization method and apparatus to analyze chemical substances by the process of emission of negatively charged particles from a heated and appropriately sensitized surface. The heated, sensitized surface is situated in a gaseous environment such that there exists around the surface a hot and possibly chemically reactive gaseous boundary layer. Sample compounds are directed to impinge into this gaseous boundary layer and onto the hot surface for the purpose of decomposing the sample compounds. Depending on the temperature of the sensitized surface and the chemical composition of the gaseous boundary layer, certain types of sample compounds form decomposition products which and highly electronegative. These electronegative species subsequently form gaseous negative ions by extracting electrons from the heated, sensitized surface. An electrical potential difference exists between the sensitized surface and a collector electrode so as to cause negative ions to move to the collector. This current of negative ions at the collector electrode is used to indicate and measure the presence of the sample compounds in question. The controllable parameters which are most critical in determining the type of samples detected are the composition of the sensitized surface, the temperature of the sensitized surface, and the chemical composition of the gaseous boundary layer. The surface temperature and boundary layer composition determine the chemical products formed in the decomposition of sample compounds. The surface temperature and the composition of the sensitized surface determine the negative charge emission characteristics of the surface.

It is a particular object of this invention to provide a method of forming a sensitized surface by mixing an alkali compound uniformly with a ceramic cement material, and using this mixture to form an alkali-ceramic bead in which there may be embedded an electrical heating coil. Being composed of a ceramic material, the resultant bead is capable of operating over a wide range of temperatures without danger of melting. In addition, the method of forming the bead is relatively simple, and allows a wide range of different ceramic-alkali compound formulations to be used. The purpose of the alkali compound is to lower the electronic work function of the ceramic so as to more easily allow the emission of negatively charged particles from the surface of the bead. Depending on the specific sample response desired, the composition of the alkali-ceramic bead may be chosen to provide the best response signal with regard to sensitivity as well as specificity.

It is also a particular object of this invention to provide a method of detecting substances containing nitrogen or phosphorus atoms with a high degree of specificity. According to this method, the alkali-ceramic bead is heated to surface temperatures in the approximate range of 600° C. to 1000° C. The bead is situated in a gaseous environment comprising an oxygen-containing gas such as air and a very dilute concentration of hydrogen ($0.05 \leq H_2/O_2 \leq 0.20$, approximately). For this mixture of gases, the boundary layer of the bead may be considered to contain radical chemical species such as H atoms, O atoms, and OH molecules similar to the chemical environment commonly found in $H_2$-air flames. However, in the present method, the concentration of $H_2$ is too low to provide a self-sustaining $H_2$-air flame, if the heating power to the bead were to be removed. In the presence of nitrogen or phosphorus compounds, this chemical environment in the boundary layer is favorable for the formation of nitrogen- or phosphorus-containing decomposition products which are highly electronegative. Although the exact identities of these electronegative species have not been firmly established, species such as CN, $NO_2$, and $PO_2$ are known to have the required electronegativity property.

It is also a particular object of this invention to provide a thermionic ionization method of detecting substances which thermally decompose into electronegative fragments in an inert chemical environment. According to this method, the alkali-ceramic bead is situated in an inert gaseous environment such as pure nitrogen. Consequently, any electronegative species that are formed are the result of the thermal decomposition chemistry involving the constituent atoms of the sample compound itself. According to this method, highly specific responses are obtained for compounds which contain $NO_2$ molecular groups, halogen atoms, or oxygen atoms. Also, according to this method, the specificity of response can be further enhanced by selecting the proper bead surface temperature for the type of response desired. For example, specific response to $NO_2$ compounds is best achieved at relatively cool bead temperatures in the approximate range of 400° C. to 600° C.

It is also a particular object of this invention to provide a thermionic ionization method for non-specific detection of hydrocarbon compounds. According to this method, the alkaliceramic bead is situated in an oxygen-containing gaseous environment with either no hydrogen present ($H_2/O_2 = 0$) or with a relatively high concentration of hydrogen ($H_2/O_2 > 0.2$, approximately). This chemical environment is favorable for the formation of decomposition products containing C and O atoms, and such species are known to be highly electronegative.

DESCRIPTION OF PREFERRED EMBODIMENT

Figure 1:
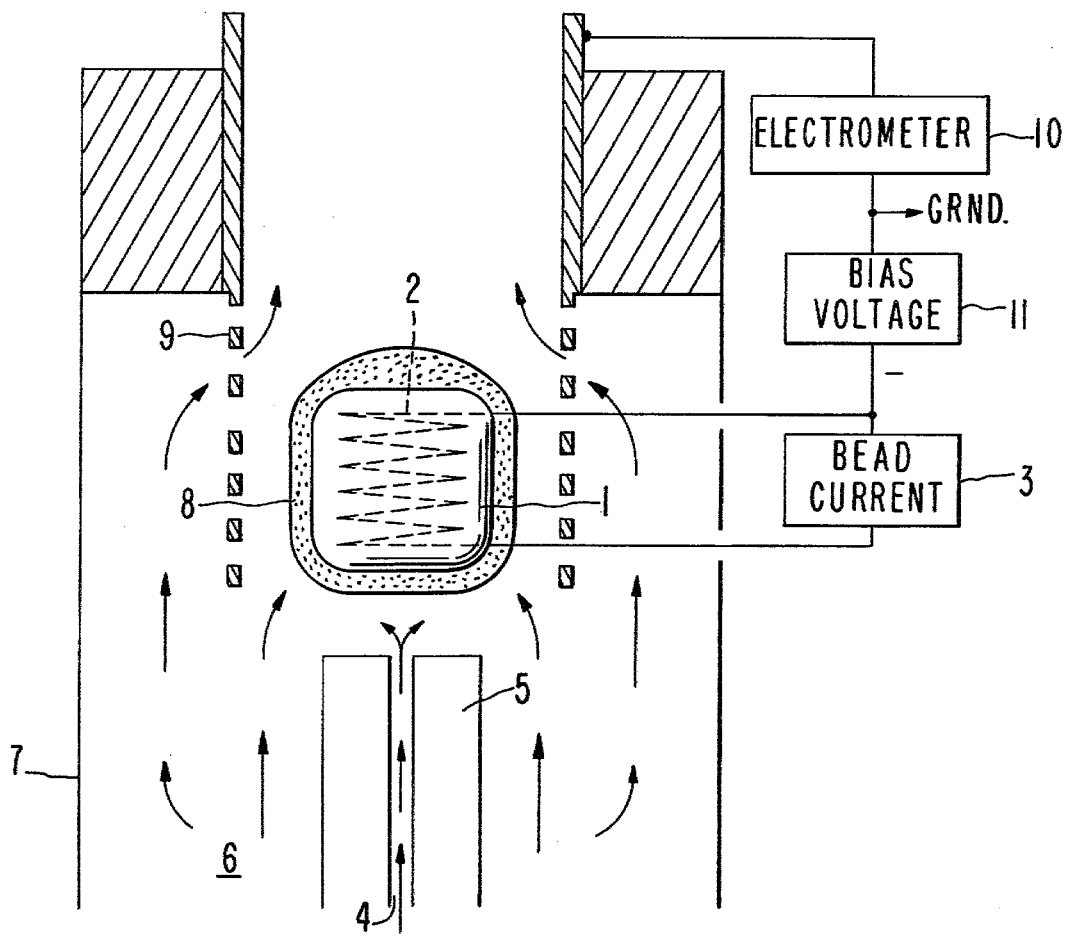
FIG. 1 is a schematic view of a selective thermionic detector according to the present invention.

FIG. 1 shows a schematic, cross-sectional view of a thermionic ionization detector according to the present invention. An alkali-ceramic bead 1 of either cylindrical or spherical shape is molded about a resistive electrical coil 2 commonly formed from either nichrome or platinum wire. The resistive coil 2 is powered by a source of electric current 3 for the purpose of heating the alkali-ceramic bead. The heated bead 1 is disposed in a gaseous environment that is generated by controllable gas flows directed to the proximity of the bead 1 via a center passageway 4 through an inner cylindrical structure 5, and via an outer annular passageway 6 between the inner cylindrer structure 5 and an outer cylindrical structure 7. The flow of gas past the hot bead forms a gaseous boundary layer 8 of high temperature, and possibly of highly reactive chemical composition.

The bead is positioned within a cylindrical electrode structure 9, which serves as a collector electrode for negatively charged ions. The collector electrode 9 is disposed coaxially within the outer cylindrical structure 7, and is perforated to permit gas glow therethrough from the outer passageway 6 into the proximity of the bead 1.

The collector electrode 9 is electrically connected to an electrometer 10, which is used to measure the magnitude of ion current collected. An electrical voltage source 11 provides a negative bias voltage to the bead 1, thereby causing negative ions formed at the bead's surface to move in a direction toward the collector electrode 9. Sample compounds are introduced to this detector along with the gas flow carried in passageway 4. The proximity of the bead 1 to the adjacent end of the cylindrical structure 5 is such that sample compounds impinge directly onto the end of the bead 1 nearest to the cylindrical structure 5.

For the embodiment illustrated in FIG. 1, suitable dimensions are as follows:

| Component | Dimensions |
|---|---|
| Bead cylinder 1 | 4-mm diameter and 4-mm height |
| Cylindrical structure 5 | 3-mm outside diameter |
| Cylindrical structure 7 | 14-mm inside diameter |
| Collector electrode 9 | 7-mm inside diameter |

For components having the above dimensions, the distance from the top of the cylindrical structure 5 to the bottom of the bead 1 is suitably 1.5 mm. These dimensions are not to be considered as restrictive; larger or smaller dimensions can be used with corresponding scaling adjustments in the gas flows.

In FIG. 1, the alkali-ceramic bead 1 is shown connected to its heating current supply by electrical connections which emanate in a direction perpendicular to the axis of the collector electrode 9. For this configuration, the collector electrode structure immediately surrounding the bead is constructed of an open, screen-like material to allow a symmetrical gas flow field surrounding the bead. In alternative embodiments, the electrical leads to the bead can extend in a direction parallel to the axis and out the top of the collector cylinder 9; and the collector electrode 9 can be formed with a completely solid cylindrical wall.

As shown in FIG. 1, the alkali-ceramic bead 1 is preferably located entirely within the collector electrode 9 so as to produce a well-defined electrical field between the concentric bead and collector structures. This relative positioning of the bead with respect to the collector minimizes the importance of precise location of the bead, and minimizes the bead bias voltage required to achieve efficient negative ion collection. In the present invention, bias voltages of −4 volts to −12 volts are commonly used, in contrast to the hundreds of volts required with prior art devices where the bead was located in an electrical fringe field.

For the specific detection of nitrogen and phosphorus compounds, typical flow rates for gases supplied to the detector are as follows:

| Gases | Flow Rates |
|---|---|
| Air through passageway 6 | 150 ml/min to 250 ml/min |
| Hydrogen through passageway 4 | 3 ml/min to 5 ml/min |
| Sample compounds contained in an inert gas such as nitrogen or helium through passageway 4 | 10 ml/min to 100 ml/min |

To obtain non-specific response to hydrocarbon compounds, the hydrogen flow is either increased to a flow rate greater than 8 ml/min or turned off altogether. To obtain responses specific to compounds containing $NO_2$ groups, halogen atoms, or other electronegative constituents, an inert gas of low thermal conductivity such as nitrogen, instead of air or hydrogen, is supplied through passageways 6 and 4. These gases and flow rates are to be considered as representative, but not restrictive. It is, of course, possible to use other types of gases than those mentioned in order to extend the specific response characteristics of a detector according to this invention.

The alkali-ceramic bead 1 is formed by mixing together proportionate amounts of an alkali compound, a ceramic cement, and water. The resultant slurry is then coated over the electrical heating coil 2 and allowed to harden. The ceramic cement preferably contains 100% inorganic constituents such as $Al_2O_3$ or $AlSiO_2$. Preferred characteristics of the ceramic cement are that it withstand temperatures in excess of 1000° C.; that it be non-porous and make gas tight seals; that it form high-strength bonds; that it resist thermal shock; and that it exhibit low shrinkage. Cements of this type are commercially available in either dry powder form or in pre-mixed, ready-to-use form. An example of a suitable ceramic cement is Super Refractory Cement C-10 manufactured by Dylon Industries, Inc. of Cleveland, Ohio.

The type of alkali compound used in forming the alkali-ceramic bead 1 depends on the intended use of the alkali-ceramic bead. Generally, it is preferable that the alkali compound have a low volatility at the desired operating temperature of the bead. Alkali surfaces have been found to be especially suitable. Other kinds of alkali compounds that might be used include alkali carbonates and alkali chlorides. For specific detection of nitrogen and phosphorus compounds, alkali-ceramic bead formulations consisting of 6% by weight of $Rb_2SO_4$ and 94% by weight of ceramic cement have exhibited excellent sample response characteristics with operating lifetimes exceeding 2000 hours.

In a thermionic detector according to this invention, the sample response currents and background currents obey the physical laws governing thermionic emission of charge from heated surfaces. According to the well-known Richardson-Dushman equation, the thermionic emission current from a hot surface is proportional to the mathematical factor $e^{-W/t}$, where W is the electronic work function of the surface and T is the surface temperature. Consequently, a graph of the logarithm of emission current versus 1/T for the alkali-ceramic bead should yield a straight line with a negative slope that is proportional to the work function. Such a plot is shown in FIG. 2 for both the background current emitted with no sample present, and for the response current to nitrogen or phosphorus compounds.

Figure 2:
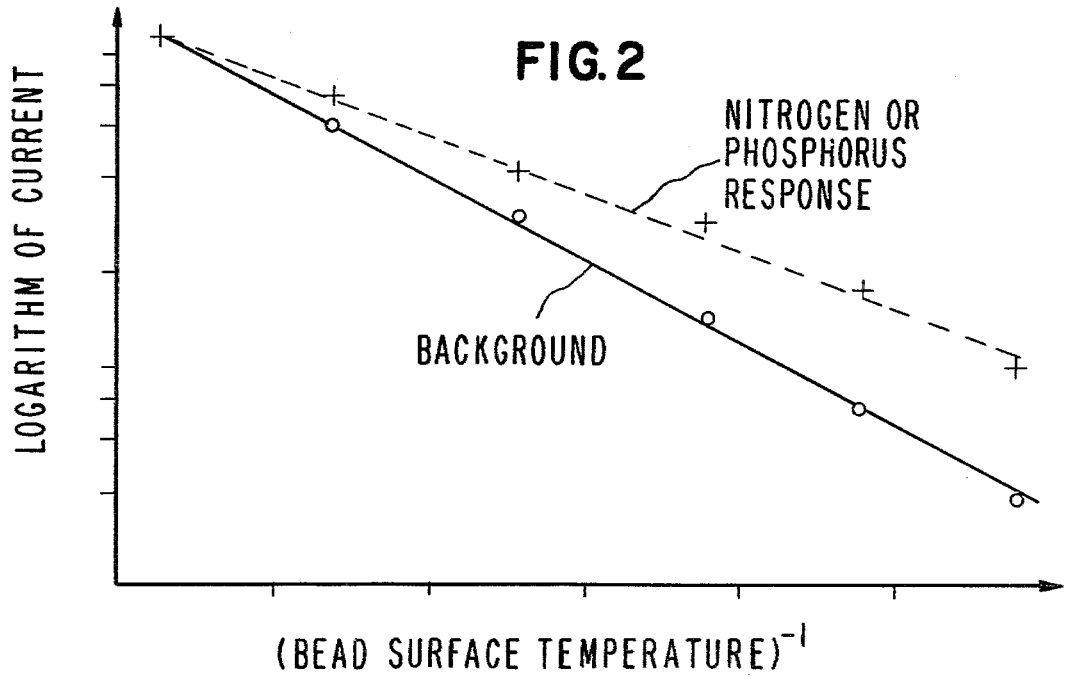
FIG. 2 is a plot of the logarithm of emission current versus the reciprocal of surface temperature for an alkaliceramic bead used in a thermionic detector according to the present invention.

FIG. 2 illustrates that both the background and response currents exhibit the dependence on bead surface temperature expected for thermionic emission. Furthermore, the difference in the slopes of the graphs for response current and for background current indicates that the response current can be viewed as being caused by a reduction of the effective work function of the bead when the bead's surface is surrounded by electronegative decomposition products of the sample.

In the present invention, the work function of the surface of the alkali-ceramic bead is dependent on both the type and density of the alkali compound used in the bead composition. Thus, for a series of beads, each of which contains the same density by volume of a different one of of the following compounds: $Na_2SO_4$, $K_1SO_4$, $Rb_2SO_4$, or $Cs_2SO_4$, the bead work function for the different beads varies in decreasing order according to $Na > K > Rb > Cs$. This is the same order as the ionization potentials of the alkali metals. Similarly, for two beads composed of two different densitites of $Rb_2SO_4$, the bead with the higher alkali density will have the lower work function. The data illustrated in FIG. 2 was obtained for a bead containing 6% by weight of $Rb_2SO_4$ and having a work function of approximately 3.4 electron volts when surrounded by the hydrogen-air gas mixture commonly used for specific nitrogen and phosphorous detection.

The emission of negative charge from the alkali-ceramic bead of this invention depends on the surface temperature of the bead as well as the work function of the bead. The surface temperaure is also important in determining the extent of decomposition of sample compounds. Consequently, enhanced sensitivity and specificity can be obtained by choosing the bead composition to give the best sample response at the desired operating temperature. For example, if the desired response requires a high surface temperature for the preferred decomposition chemistry, then a bead of relatively low work function may provide too large a background current in comparison to the sample current. In that case, better response is obtained by using a bead composition of higher work function. Similarly, specific responses requiring relatively low surface temperatures would be expected to be optimized by using bead compositions of relatively low work function.

An alkali-ceramic bead according to this invention can be an abundant source of positive ion current, if it is biased at a positive voltage with respect to the collector electrode. However, positive ion operation is generally characterized by very low sample response and very high background. Therefore, negative ion operation generally is superior in providing the desirable combination of high sample response and low background.

This invention has been described in terms of a preferred embodiment. It is to be recognized, however, that variations in the composition of the alkali-ceramic bead and modifications in the configuration of the thermionic detector apparatus might be appropriate for certain applications and yet be within the scope of the invention. Accordingly, this invention is to be broadly construed, and is limited only by the following claims.

What is claimed is:

1. A mehod for analyzing a sample to detect the presence of a component of said sample, said method comprising the steps of:
    (a) electrically heating in a gaseous environment and to operating temperatures within the approximate range 400° C. to 1000° C. a solid body comprising a hardened ceramic cement impregnated with an alkali metal, and capable of withstanding operating temperatures in excess of 1000° C.;
    (b) causing said sample to interact with said heated body to form negative ions,
    (c) maintaining a difference of electrical potential between said surface of said body and a collector electrode to cause a current of said negative ions to move towards said collector electrode, and
    (d) measuring said negative ion current to detect the presence of said specific component of said sample.

2. The method of claim 1 wherein said body is impregnated with a single metal selected from the group consisting of sodium, potassium, rubidium and cesium.

3. The method of claim 1 wherein said heating is performed in a gaseous environment maintained by gas flow directed toward the surface of said body.

4. The method of claim 3 wherein said heating is performed in said gaseous environment comprising a gas flow of separate controllable streams of gases.

5. The method of claim 4 wherein said heating is performed in said gaseous environment comprising a gas flow of separate streams of gases, said gases mixing in the vicinity of the surface of said body.

6. The method of claim 5 wherein a first stream of gas and a second stream of gas are directed toward said surface of said body, said first stream comprising nitrogen, and said second stream comprising hydrogen and an inert carrier gas, said sample being carried by said inert gas to the vicinity of said surface of said body.

7. The method of claim 5 wherein a first stream of gas and a second stream of gas are directed toward said surface of said body, said first stream comprising a gas containing molecular oxygen, and said second stream comprising hydrogen and an inert carrier gas, said sample being carried by said inert gas to the vicinity of said surface of said ceramic body.

8. The method of claim 7 wherein said first stream comprises air.

9. The method of claim 1 wherein said step of causing said sample to interact with said body is accomplished by introducing said sample into a stream of gas directed toward said surface of said body.

10. The method of claim 9 wherein said step of heating said body generates a gaseous boundary layer adjacent said surface of said body, and wherein said step of causing said sample to interact with said surface of said body causes said sample to interact also with chemical species in said gaseous boundary layer to form reaction products that are ionizable at said surface of said body.

11. The method of claim 1 wherein said step of maintaining a difference of electrical potential between said surface of said body and said collector electrode is accomplished by applying a negative bias voltage to said ceramic body.

12. The method of claim 11 wherein said body is disposed with respect to said collector electrode so as to produce a well-defined electrical field therebetween.

13. The method of claim 1 wherein said step of measuring said negative ion current is accomplished by means of an electrometer connected to said collector electrode.

14. The method of claim 1 wherein said component of said sample whose presence is to be detected is nitrogen.

15. The method of claim 1 wherein said component of said sample whose presence is to be detected is phosphorus.

16. The method of claim 1 wherein said component of said sample whose presence is to be detected is a compound containing an electronegative constituent.

17. The method of claim 16 wherein said component of said sample whose presence is to be detected is a compound containing a halogen atom.

18. The method of claim 16 wherein said component of said sample whose presence is to be detected is a compound containing an $NO_2$ group.

19. The method of claim 1 wherein said component of said sample whose presence is to be detected is a hydrocarbon compound whose presence is to be non-specifically detected.

20. An apparatus for the analysis of a sample in a gaseous state to detect the presence of a specific component of said sample, said apparatus comprising:
   a solid body comprising a hardened ceramic cement impregnated with an alkali metal, said solid body being capable of withstanding operating temperatures in excess of 1000° C., electrical heating means for internally heating said body in a gaseous environment to cause said body to operate at temperatures in the approximate range of 400° C. to 1000° C.,
   means for transferring said gaseous sample about said body whereby said sample interacts with said body to form negative ions in response to the presence of said specific component in said gas,
   means for causing a current of said negative ions to move toward a collector electrode,
   and means for measuring said negative ion current, whereby said specific component is detected.

21. The apparatus of claim 20 wherein said body is impregnated with a single metal selected from the group consisting of sodium, potassium, rubidium and cesium.

22. The apparatus of claim 20 wherein said body comprises an bead that is molded about an electrically resistive coil.

23. The apparatus of claim 22 wherein said bead is of generally cylindrical configuration.

24. The apparatus of claim 22 wherein said bead is of generally spherical configuration.

25. The apparatus of claim 22 wherein said electrically resistive coil is formed of nichrome wire.

26. The apparatus of claim 22 wherein said electrically resistive coil is formed of platinum wire.

27. The apparatus of claim 22 wherein said means for heating said bead comprises means for applying an electric current to said electrically resistive coil.

28. The apparatus of claim 20 wherein said gaseous environment is established by means for directing a gas flow towards said body.

29. The apparatus of claim 28 wherein said means for directing a gas flow directs separate controllable streams of gases.

30. The apparatus of claim 29 wherein said means for directing a gas flow causes said separate streams of gases to mix in the vicinity of said surface of said body.

31. The apparatus of claim 29 wherein said means for directing separate controllable streams of gases comprises an inner cylindrical structure and an outer cylindrical structure, said inner cylindrical structure being disposed within said outer cylindrical structure, one gas stream passageway being formed within said inner cylindrical structure, and another gas stream passageway being provided by an annular region between said inner cylindrical structure and said outer cylindrical structure.

32. The apparatus of claim 31 wherein said collector electrode is of generally cylindrical configuration and is disposed within said outer cylindrical structure along the axis of and spaced apart from said inner cylindrical structure.

33. The apparatus of claim 32 wherein the interior of said cylindrical collector electrode provides a passageway for gas flow away from the vicinity of said body.

34. The apparatus of claim 32 wherein said body is disposed entirely within the interior of said collector electrode, whereby a well-defined electric field can be maintained between said body and said collector electrode.

35. The apparatus of claim 37 wherein a portion of said collector electrode is perforated to permit gas flow therethrough to the vicinity of said body.

36. The apparatus as in claim 20 in which said solid body withstands said operating temperatures without softening or melting.

37. The apparatus as in claim 36 in which said ceramic cement comprises $Al_2O_3$.

38. The apparatus as in claim 36 in which said ceramic cement comprises $AlSiO_2$.

39. The apparatus of claim 1 in which said body comprises approximately 94% by weight of said ceramic cement, and approximately 6% by weight of a compound of said alkali metal.

40. An apparatus as in claim 1 in which said means for heating said alkali impregnated body in a gaseous environment generates a gaseous boundary layer adjacent a surface of said body,
   and in which said means for transferring said sample causes said sample to react with said surface in said gaseous boundary layer to form said negative ions.

41. The apparatus of claim 40 wherein said means for transferring said gaseous sample causes said sample to interact also with chemical species in said gaseous boundary layer to form reaction products that are ionizable at said surface of said body.

42. An apparatus for the specific detection of a component in a sample, said apparatus comprising:
   a solid body comprising a hardened ceramic cement impregnated with an alkali metal, said ceramic cement including a material selected from the group consisting of $Al_2O_3$ and $AlSiO_2$, said solid body maintaining its structural integrity as a solid at temperatures in excess of 1000° C.,
   means for maintaining a gaseous environment adjacent said solid body, said gaseous environment comprising a mixture of hydrogen and a gas-containing molecular oxygen, electrical means embedded in said solid body for heating said solid body in said gaseous environment to generate a gaseous boundary layer adjacent a surface of said body, means for causing said sample to interact with said surface and with chemical species in said gaseous boundary layer, the interaction of said sample with said chemical species in said boundary layer forming reaction products that interact with said surface, whereby negative ions are formed from the interactions of said sample and of said reaction products with said surface, means for causing a current of said negative ions to move toward a collector electrode, and means for measuring said negative ion current.

43. The apparatus of claim 42 wherein said means for causing said sample to interact with said surface and with chemical species in said gaseous boundary layer comprises means for transporting said sample toward said surface in a flow of inert gas.

44. The apparatus of claim 42 wherein said means for maintaining said gaseous environment adjacent said body is adjustable to provide a desired ratio of hydrogen to oxygen in said gaseous environment.

45. The apparatus of claim 42 wherein said means for maintaining said gaseous environment adjacent said body provides a ratio of hydrogen to oxygen in said gaseous environment that is appropriate for the specific detection of nitrogen.

46. The apparatus of claim 42 wherein said means for maintaining said gaseous environment adjacent said body provides a ratio of hydrogen to oxygen in said gaseous environment that is appropriate for the specific detection of phosphorus.

47. An apparatus for the analysis of a gaseous sample to detect the presence of a specific component of said sample, said apparatus comprising:

a solid body comprising a hardened ceramic cement impregnated with an alkali metal, said solid body being capable of withstanding operating temperatures in excess of 1000° C. without softening or melting, said metal being selected from the group consisting of sodium, potassium, rubidium, and cesium;

electrical means embedded in said solid body for heating said body in a flowing gaseous environment comprising hydrogen and molecular oxygen to cause said solid body to operate at temperatures in the approximate range of 400° C. to 1000° C.;

means for directing said gaseous sample into said flowing gaseous environment and into interaction with said alkali-impregnated solid body, negative ions being formed in said environment in response to the presence of said specific component in said sample;

means for detecting and measuring said negative ions, whereby said component may be detected.

48. Apparatus as in claim 47 in which said alkali metal is rubidium.

49. Apparatus as in claim 48 in which said rubidium is present in the form of the compound rubidium sulfate.

50. Apparatus as in claim 48 in which said alkali metal is in the form of an alkali compound selected from the group consisting of alkali sulfates, alkali carbonates, and alkali chlorides.

51. Apparatus as in claim 48 in which said ceramic cement comprises approximately 94% by weight of said solid body, and said alkali metal comprises 6% by weight of said solid body.

52. Apparatus as in claim 51 in which said alkali metal is in the form of rubidium sulfate.

53. Apparatus as in any one of the claims 47 through 52 in which said ceramic cement comprises $Al_2O_3$.

54. Apparatus as in any one of the claims 47 through 52 in which said ceramic cement comprises $AlSiO_2$.

* * * * *